United States Patent
Wight et al.

(10) Patent No.: US 12,049,095 B2
(45) Date of Patent: Jul. 30, 2024

(54) ANTIMICROBIAL MEDICAL GLOVE PRINTING METHOD

(71) Applicant: Chemical Intelligence Limited, Cambridge (GB)

(72) Inventors: Paul Wight, Manchester (GB); Robert Gros, Cambridge (GB)

(73) Assignee: BMG (British Medical Group) Limited, Cambridge (GB)

(*) Notice: Subject to any disclaimer, the term of this patent is extended or adjusted under 35 U.S.C. 154(b) by 172 days.

(21) Appl. No.: 17/624,146

(22) PCT Filed: Jul. 1, 2020

(86) PCT No.: PCT/EP2020/068559
§ 371 (c)(1),
(2) Date: Dec. 30, 2021

(87) PCT Pub. No.: WO2021/001442
PCT Pub. Date: Jan. 7, 2021

(65) Prior Publication Data
US 2022/0356364 A1     Nov. 10, 2022

(30) Foreign Application Priority Data
Jul. 1, 2019 (EP) .................................... 19183702

(51) Int. Cl.
*B41M 5/00* (2006.01)
*B41M 1/40* (2006.01)

(52) U.S. Cl.
CPC ........ *B41M 5/0088* (2013.01); *B41M 5/0023* (2013.01); *B41M 5/0047* (2013.01); *B41M 1/40* (2013.01)

(58) Field of Classification Search
CPC ............ B41M 5/0088; B41M 5/0023; B41M 5/0047; B41M 1/40
USPC ......................................................... 428/32.1
See application file for complete search history.

(56) References Cited

U.S. PATENT DOCUMENTS

| | | | |
|---|---|---|---|
| 5,486,274 | A | 1/1996 | Thetford et al. |
| 2003/0157150 | A1 | 8/2003 | Lee |
| 2009/0235429 | A1 | 9/2009 | Pickard et al. |
| 2010/0221307 | A1 | 9/2010 | Matsushita et al. |
| 2012/0056929 | A1* | 3/2012 | Sao ...................... C09D 11/322 524/220 |
| 2016/0058921 | A1* | 3/2016 | Gros ......................... C08J 5/02 264/306 |
| 2016/0159992 | A1 | 6/2016 | Foo et al. |

(Continued)

FOREIGN PATENT DOCUMENTS

| | | |
|---|---|---|
| CN | 1189987 A | 8/1998 |
| CN | 104910553 A | 9/2015 |

(Continued)

OTHER PUBLICATIONS

Machine Translation of CN 115464988 A. (Year: 2022).*

(Continued)

*Primary Examiner* — Betelhem Shewareged
(74) *Attorney, Agent, or Firm* — Foley Hoag LLP; David P. Halstead

(57) ABSTRACT

A printing process for printing with ink an image on an antimicrobial medical glove formed by a dipping process, wherein the image is first printed on a former and transferred to the glove during dipping.

19 Claims, 2 Drawing Sheets

(56) References Cited

U.S. PATENT DOCUMENTS

| | | | | |
|---|---|---|---|---|
| 2018/0105710 A1* | 4/2018 | Hong | ................. | C09D 11/328 |
| 2022/0356364 A1* | 11/2022 | Wight | ................. | B29C 37/0032 |
| 2022/0386724 A1 | 12/2022 | Wilkinson et al. | | |
| 2023/0147289 A1 | 5/2023 | Wight | | |

FOREIGN PATENT DOCUMENTS

| | | | | | |
|---|---|---|---|---|---|
| CN | 115464988 A | * | 12/2022 | ................. | B41J 2/01 |
| EP | 0815880 A2 | | 1/1998 | | |
| JP | H05147127 A | | 6/1993 | | |
| JP | 2005/009065 A | | 1/2005 | | |
| JP | 2007/118252 A | | 5/2007 | | |
| JP | 5885917 B2 | | 3/2016 | | |
| WO | WO-93/00815 A1 | | 1/1993 | | |
| WO | WO-98/30094 A1 | | 7/1998 | | |
| WO | WO-99/49823 A1 | | 10/1999 | | |
| WO | WO-2010/118180 A1 | | 10/2010 | | |
| WO | WO-2010/138426 A1 | | 12/2010 | | |
| WO | WO-2015/154543 A1 | | 10/2015 | | |
| WO | WO-2017/148957 A1 | | 9/2017 | | |
| WO | WO-2018/091774 A1 | | 5/2018 | | |

OTHER PUBLICATIONS

JPH05147127A Eng. Translation (Year: 1993).*
Extended European Search Report for EP Application No. 19183702.0 dated Feb. 6, 2020.
International Search Report and Written Opinion and International Application No. PCT/EP2020/068559 dated Oct. 13, 2020.
Extended European Search Report for EP Application No. 19183703.8 dated Jan. 17, 2020.
Extended European Search Report for EP Application No. 19183704.6 dated Jan. 8, 2020.
Extended European Search Report for EP Application No. 19187301.2 dated Jun. 26, 2020.
Hamdi et al., "Synthesis of Novel Antibacterial Metal Free and Metallophthalocyanines Appending With Four Peripheral Coumarin Derivatives and Their Separation of Structural Isomers," Heterocycles, 87(11): 2283 (2013).
International Search Report and Written Opinion and International Application No. PCT/EP2020/068558 dated Sep. 4, 2020.
International Search Report and Written Opinion and International Application No. PCT/EP2020/068562 dated Sep. 23, 2020.
International Search Report and Written Opinion and International Application No. PCT/EP2020/068568 dated Nov. 25, 2020.
Saki et al., "Synthesis and characterization of novel quaternized 2, 3- (diethylmethylamino)phenoxy tetrasubstituted Indium and Gallium phthalocyanines and comparison of their antimicrobial and antioxidant properties with different phthalocyanines," Inorganic Chemistry Communications, 95: 122-129 (2018).

* cited by examiner

ANTIMICROBIAL MEDICAL GLOVE PRINTING METHOD

CROSS-REFERENCE TO RELATED APPLICATION

This application is a National Stage Application of International Patent Application No. PCT/EP2020/068559, filed Jul. 1, 2020, which claims the benefit of European Application No.: 19183702.0, filed Jul. 1, 2019.

FIELD OF THE INVENTION

The present invention relates to a method for printing an image on a glove, and an antimicrobial glove obtainable from said process.

BACKGROUND OF THE INVENTION

Glove printing is known for example from CN201711106062 and JP2007118252. Conventional gloves, including medical examination gloves may be printed in two conventional ways. In the first, the glove is printed after formation, in an offline processing method. In this process the glove is first completed and stripped from the former, during which it is turned inside out. Once the completed glove has been made and the glove stripped from the former, the item can be printed by conventional means, such is ink jet or screen printing. The disadvantage of this is that the printing is done offline from the glove forming process, which is inefficient, and the printing is done on a flexible and generally non-flat surface which can decrease quality of print.

The second method of creating images on gloves is to ink jet print on the surface of the glove still on the former. This process can be done online during glove manufacture, but it results in an image or text only on the inner surface of the glove as the glove is turned inside out on stripping. This reduces the utility of the marking because it is inherently less visible.

Both these methods are inefficient and costly or have poor image quality due to the way the image is produced on the glove surface directly, or on the wrong side. Hence, there remains a need for another method of creating images and text on gloves made from a former process, such as nitrile, natural rubber and nitrile rubber.

JPH05147127 describes a printing process for printing on a glove former using a rubber stamp method. However, this is for thick household gloves rather than medical examination gloves.

SUMMARY OF THE INVENTION

The present invention provides a printing process for printing ink on a glove formed by a dipping process, wherein the image is first printed on the former and transferred to the glove during dipping. Preferably the glove is an antimicrobial medical glove e.g. a medical examination or surgical glove.

The present invention further provides an antimicrobial glove obtainable by the printing process of the present invention.

Printing on the former results in an image on the glove outer surface. Printing can be done rapidly and cheaply during manufacture of the article, rather than offline in a separate step.

DETAILED DESCRIPTION OF THE INVENTION

Figure 1:
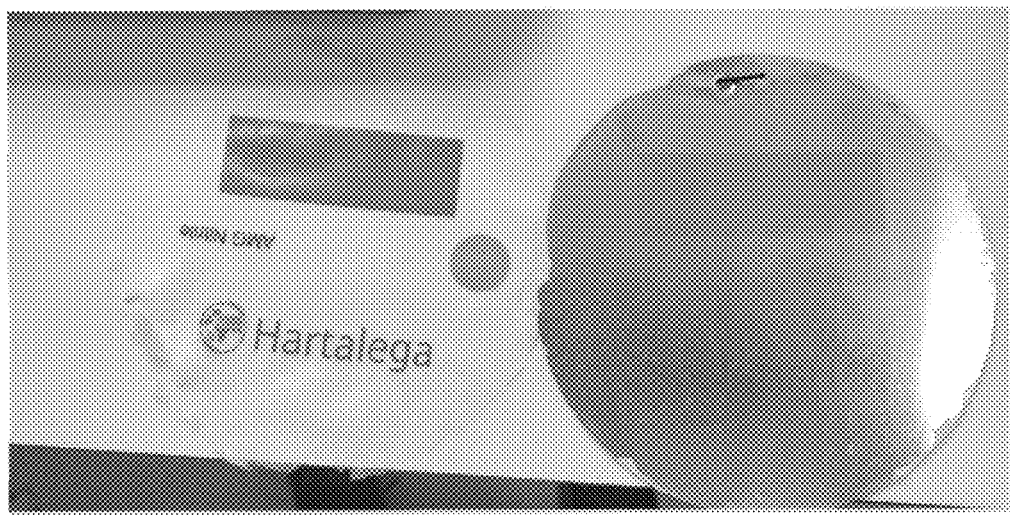
FIG. 1 shows a printed nitrile sample.

The present invention is directed towards methods for forming a glove with an image or text on the outer surface as used. It comprises the steps of printing an ink onto the former used to create the glove. The printing process is ink jet. Preferably this printing process is done after the former is cleaned, and after it is dipped in any coagulant solution required, containing typically a coagulant and mold release agent, such as calcium nitrate and calcium stearate. The printing process is preferably done on the former in the final step before dipping or coating with polymer. Typical polymers for glove formation can be used, such as PVC, natural rubber, isoprene, nitrile rubber. Preferably the printing is done on the coagulant coated former while it is still hot, preferably 30-60° C.

During this process the ink on the former is transferred to the polymer. The film covering the former thereby absorbs the ink on the former, the ink becoming part of the glove. After curing and drying of the film, the glove can be stripped from the former, turning it inside out, thereby moving the image to the outside of the glove. This creates a high speed, high efficiency printing process for rubber gloves of all kinds, and other items that are made by a similar process, of film formation on a former, followed by stripping from a former.

In this process, it is important that the ink printed on the former is efficiently transferred into the film used to form the glove. Inefficient transfer may lead to poor image quality, or contamination of the former by residual ink. The ink can be chosen carefully to give good image quality.

The types of inks that can be used in this process are described below, together with the criteria with which they can be selected.

The simplest inks are water soluble dyes. The inks may also typically comprise surfactant, and cosolvents such as alcohols and ethers. Anionic dyes are the simplest and are especially preferable when printing on formers that are previously coated with coagulant solution such as calcium nitrate. The calcium nitrate coating on formers, used for such gloves as natural rubber and nitrile is especially beneficial to the printing process, because it fixes the anionic dyes on the surface of the former, by forming insoluble calcium/dye salts. It is beneficial to select dyes that have a well established safety profile, such as food colorants. These include but are not limited to Allura Red, Brilliant Blue FCF, Erythrosine, Fast Green FCF, Indigo Carmine, Sunset Yellow FCF, Tartrazine. A second type of water soluble dye that is preferred is cationic dyes. These are preferred because they bind to anionically stabilised polymers such as natural rubber and nitrile. These polymers contain some anionic groups, which are capable of binding the cationic dues, thereby preventing them from leaching out of the glove during use.

A second type of ink is a pigmented ink. In pigmented inks the colorant is an insoluble colourant particle. Any type of pigment ink can be used, but preferable are those typically used in ink jet printing containing finely dispersed particles of pigments such as Pigment Blue 15.3 or 15.4, Pigment Red 122, Pigment Red 146, Pigment Red 147, Pigment Red 202, Pigment Violet 19, Pigment Yellow 155 or Pigment Yellow 74. These pigments are stabilised by dispersants. Typical inks made like this are very sensitive to calcium salts, whereby they are rapidly precipitated and fixed, making them especially suited to printing on formers coated with coagulant such as calcium nitrate. Other pigments that are especially suitable are those used in the coloration of gloves themselves.

A third type of ink that can be used is inks that are themselves formulated with latexes as fixing agents. These inks are known in ink jet printing, and are especially suited to this printing process because the ink becomes part of the glove and cannot be removed. These inks are described in patents such as U.S. Pat. No. 5,977,210, U.S. Pat. No. 20070216742, EP 1561788, EP 1074589, U.S. Pat. No. 6,184,268

A fourth type of ink especially suitable to this printing process is to use the latex or solution that is composed of the same material as the glove is formed from, such as nitrile latex or natural rubber latex, or PVC. The ink must be formulated for the printing process, so if for example it is being jetted, the components must typically be diluted with a solvent such as water or organic solvent. Usually this means achieving a surface tension of 25-40 dyne/cm and a viscosity of 3-15 centipoise. Especially preferably a nitrile glove can printed with a nitrile latex, and a PVC glove with a PVC containing ink. The colorants are pigments or dyes that are typically used for these gloves, or are typically used in ink jet as described as above.

A fifth type of ink that can be used in this process is solvent based inks, preferably alcohol based inks, containing either solvent soluble dyes or pigment dispersions.

In some gloves, colorants are already added to create a colored glove. In such cases the image quality from our process can be improved by having an underprint of white ink. To realise this under printing, the white can be overprinted on the image printed on the former, because the order of printing is reversed due to the way the ink is transferred onto the glove. White inks can be formulated from titanium dioxide for example. The white ink may also contain latex, such as those used in ink jet, or those used in glove formation.

Preferably the former used in the process of the present invention is coated with a coagulant. The preferred coagulant is calcium nitrate. The coagulant makes the ink coagulate quickly. Pigment inks coagulate better because they are sensitive to calcium or other salts. For latex inks, the coagulant's normal function is to coagulate the latex particles into a film before curing to create an elastomeric article. In the present invention the coagulant on the former can be used to create a secondary function capable for coagulating ink as well as for example latexes. This makes the coagulant coated former an ideal printing substrate because the ink coagulates very rapidly on the surface of the former. Only a small portion of the coagulant is used to coagulate the ink film which is very thin. The ink film is then transferred into/onto the film, for example a latex film.

The image is produced on the outer surface of a glove because it is inverted on stripping. This results in higher image quality because the image is not seen through a film, such as a latex film which scatters light. The coagulant on the former is now dual purpose, to coagulate the ink to create a high quality image on the former surface without running or smearing, and to coagulate the latex.

One of the most significant advantages of the ink jet printing process of the present invention is that it can be used for many types of gloves. For example, in manufacture of nitrile medical examination gloves and natural rubber gloves, the former can be first dipped in a coagulant solution which can be composed of calcium nitrate and mold release agent of calcium stearate. The coagulant is dried on the former, and then dipped in nitrile or natural rubber latex. The function of the coagulant is to coagulate a thin layer of water dispersed polymer, the latex, on the former, after which the polymer film is cured and dried in an oven to make the glove elastic. However, in order to achieve this a very thin and controlled layer of coagulant is preferred for the glove mold surface. In such an example where coagulant is used, if the coagulant layer is disturbed before dipping in the nitrile or natural rubber latex this prevents glove formation, because coagulant on the surface is used to make a film, before curing.

Therefore, contact printing processes are ineffective, whereas ink jet is able to print on the surface of the former without touching it. The great advantage of this is print quality, because if the printing process is done as described, a wide variety of glove types can be made, with the print now appearing on the outer surface of the glove after stripping, which turns the glove inside out.

The uses for the printing are not limited by the printing described, but may be used for branding of gloves, reminder messages on the gloves, such as for example, "hand hygiene moments" as used in hospitals, and theft protection by marking gloves. Functional materials as well as simple images and text may also be printed on to the surface of the gloves by this method, such as electrical conduction improvers, tribology and friction improvers, antimicrobials, building up multiple layers of materials by printing on the former, or other functional substances which may be required on the article surface.

While the invention has been described in terms of what is presently considered to be the most practical and preferred embodiments, it is to be understood that the invention needs not be limited to the disclosed embodiments. On the contrary, it is intended to cover various modifications and similar arrangements included within scope of the appended claims which are to be accorded with the broadest interpretation so as to encompass all such modifications and similar structures.

The present invention will now be illustrated, but in no way limited, by reference to the following examples.

EXAMPLES

Latex type ink from an HP 821 cartridge was used in an Epson XP830 ink jet printer.

As a model for transfer, an aluminium disc of 120 mm diameter was used. The disc was dipped in a coagulant solution of 15% calcium nitrate, 0.8% calcium stearate dispersion. The coagulant was dried on the disc in an oven at 60° C. A mirror image print was then printed on the disc using the XP830 printer. The disc was then dipped in a nitrile latex dispersion, cured in an oven at 120° C. for 20 minutes and removed. The print transferred almost completely to the nitrile and could not be removed from the nitrile elastomer. The disc was easily washed in water for subsequent transfers. The printed nitrile obtained can be seen in FIG. 1.

In another series of experiments it is also confirmed ink jet is much superior to pad printing for printing on the outer surface of gloves. A 6 kg solution of coagulant was prepared from calcium nitrate crystals (1020 g), calcium stearate dispersion (40%), 105 g and water 4875 g. A former at 50° C. was dipped and withdraw to produce a coagulant coated former, which was dried in an oven at 60° C. The former was then printed on, with a stamp of dimensions 2 cm×2.5 cm. The same ink over the same area was applied by ink jet process, in the same size, by cutting a template from the stamp, and jetting through it to produce an image of the same size. The formers were immediately dipped into nitrile latex, Nantex 6730, and cured in an oven at 120° C. for 20 minutes.

Figure 2:
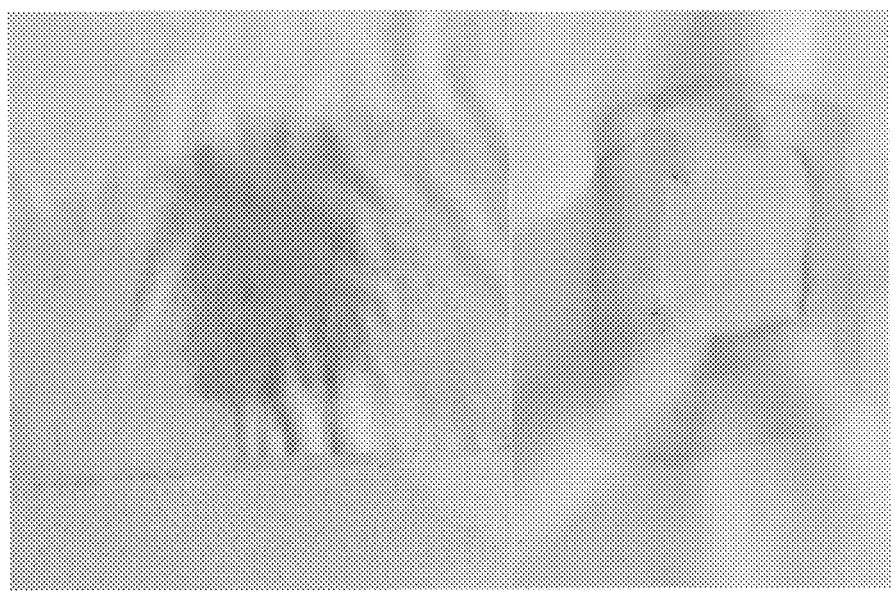
FIG. 2 shoes stamp printing on the left-hand side and ink jet printing on the right-hand side.
Figure 3:
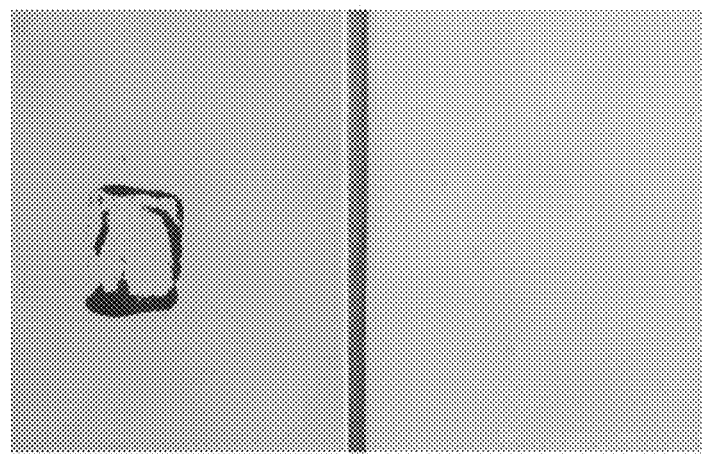
FIG. 3 shows stamp printed residual ink (left-hand side) and ink jet printed (right-hand side) on porcelian former.

FIG. 2 shows stamp printing on the left side and ink jet printing on the right hand side. FIG. 3 shows stamp printed residual ink (left hand side) and ink jet printed (right hand side) on porcelain former.

After stripping, the stamp printed film could be seen to be damaged and had a hole where the stamp had been applied, because the coagulant film had been disturbed. This is due to the liquid ink on the stamp re-dissolving the calcium nitrate and pushing it to the edges of where the stamp had been pressed. The jet printed film however was still perfect. This could be confirmed by weighing the overall weight of the film produced by the two processes with results as shown in the table below.

| Printing Method | Total Film Weight after drying and curing |
|---|---|
| Stamp printing | 1.0685 |
| Jet printing | 1.1705 |

The stamp printed method reduced the film weight by approximately 10%, due to the hole where the print was applied. It should also be noted that this process is also applicable to PVC gloves where no coagulant is present on the former.

The invention claimed is:

1. An ink jet printing process for printing with ink an image on a glove formed by a dipping process, wherein the image is first printed on a former and transferred to the glove during dipping, wherein the film covering the former absorbs the ink on the former.

2. The printing process according to claim 1, wherein the ink is an aqueous ink comprising anionic dyes, optionally food dyes.

3. The printing process according to claim 1, wherein the ink is an aqueous ink comprising cationic dyes.

4. The printing process according to claim 1, wherein the ink is an aqueous ink comprising pigment colorants.

5. The printing process according to claim 4, wherein the ink comprises any of Pigment Blue 15.3 or 15.4, Pigment Red 122, Pigment Red 146, Pigment Red 147, Pigment Red 202, Pigment Violet 19, Pigment Yellow 155, Pigment Yellow 74A, Pigment Black 7 or Titanium dioxide.

6. The printing process according to claim 1, wherein the ink is an aqueous ink comprising latex.

7. The printing process according to claim 6, wherein the ink is an aqueous ink comprising synthetic latexes.

8. The printing process according to claim 1, wherein the ink is a solvent based ink comprising pigments.

9. The printing process according to claim 1, wherein the ink is a solvent based ink comprising pigments and PVC.

10. The printing process according to claim 1, wherein the ink is solvent based, comprising either solvent soluble dyes or pigment dispersions.

11. The printing process according to claim 1, wherein the ink is an aqueous ink comprising any of antistatic coatings, biocides, or magnetic materials to be deposited onto the surface of a glove formed by dipping.

12. A printing process according to claim 1, wherein the glove comprises nitrile, natural rubber latex, vinyl, isoprene or neoprene.

13. A printing process according to claim 1, wherein the former is coated with a coagulant.

14. The printing process according to claim 13, wherein the coagulant comprises calcium nitrate.

15. The printing process according to claim 13, wherein the former is dipped in coagulant solution comprising calcium nitrate and calcium stearate.

16. The printing process according to claim 1, wherein the glove is an antimicrobial glove.

17. An antimicrobial glove obtainable by the process according claim 1.

18. A printing process according to claim 1, wherein the ink is an aqueous ink comprising nitrile latex, natural rubber latex, neoprene or isoprene.

19. A printing process according to claim 1, wherein the ink is an alcohol based ink, comprising either solvent soluble dyes or pigment dispersions.

* * * * *